(12) United States Patent
Craig

(10) Patent No.: US 9,554,820 B2
(45) Date of Patent: Jan. 31, 2017

(54) ULTRASONIC SURGICAL INSTRUMENT

(75) Inventor: Jason L. Craig, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 494 days.

(21) Appl. No.: 13/486,129

(22) Filed: Jun. 1, 2012

(65) Prior Publication Data

US 2013/0325047 A1 Dec. 5, 2013

(51) Int. Cl.
*A61B 17/32* (2006.01)
*A61B 17/29* (2006.01)

(52) U.S. Cl.
CPC .. *A61B 17/320092* (2013.01); *A61B 2017/293* (2013.01); *A61B 2017/2929* (2013.01)

(58) Field of Classification Search
CPC .............. A61B 17/320092; A61B 2017/2929; A61B 2017/293; A61B 2017/00477; A61B 17/320068
USPC ..... 606/169, 45, 99, 1, 40, 171, 174, 79–85, 606/167, 170, 205–209; 83/698.41, 956
See application file for complete search history.

(56) References Cited

U.S. PATENT DOCUMENTS

| | | | |
|---|---|---|---|
| 4,535,759 A | 8/1985 | Polk et al. | |
| 5,318,570 A | 6/1994 | Hood et al. | |
| 5,342,362 A | 8/1994 | Kenyon et al. | |
| 5,776,155 A * | 7/1998 | Beaupre et al. | 606/169 |
| 5,893,835 A | 4/1999 | Witt et al. | |
| 6,063,050 A | 5/2000 | Manna et al. | |
| 8,882,750 B2 * | 11/2014 | Stefan et al. | 606/1 |
| 2011/0004222 A1 | 1/2011 | Biedermann et al. | |
| 2011/0190832 A1 | 8/2011 | Taylor et al. | |
| 2012/0078278 A1 * | 3/2012 | Bales et al. | 606/169 |

FOREIGN PATENT DOCUMENTS

JP 2000237204 9/2000

OTHER PUBLICATIONS http://dictionary.reference.com/browse/lock.*
U.S. Appl. No. 13/108,117, filed May 16, 2011, Andrey Balanev.
U.S. Appl. No. 13/149,570, filed May 31, 2011, William N. Gregg.
U.S. Appl. No. 13/189,670, filed Jul. 25, 2011, Sean T. Dycus.
U.S. Appl. No. 13/248,402, filed Sep. 29, 2011, Stoddard et al.
U.S. Appl. No. 13/294,743, filed Nov. 11, 2011, Misuchenko et al.
U.S. Appl. No. 13/360,910, filed Jan. 30, 2012, Balanev et al.
U.S. Appl. No. 13/435,765, filed Mar. 30, 2012, Anthony B. Ross.
U.S. Appl. No. 13/435,835, filed Mar. 30, 2012, Anthony B. Ross.
U.S. Appl. No. 13/435,922, filed Mar. 30, 2012, Anthony B. Ross.

(Continued)

*Primary Examiner* — Kathleen Holwerda
*Assistant Examiner* — Socrates L Boutsikaris

(57) ABSTRACT

An ultrasonic surgical instrument is provided and includes a housing. A shaft is supported on the housing and defines a longitudinal axis therethrough. The shaft supports a jaw member at a distal end thereof. The jaw member is movable between open and clamping configurations. A probe includes proximal and distal ends. The distal end has an active blade thereon configured to effect tissue when the jaw member is in the clamping configuration. The proximal end has at least one mating feature thereon. A rotating assembly operably supported on the housing is configured to rotate the shaft. The rotating assembly includes a torque adapter that is engageable with the at least one mating feature to selectively and releasably couple the probe to the housing.

13 Claims, 4 Drawing Sheets

(56) References Cited

OTHER PUBLICATIONS

U.S. Appl. No. 13/435,062, filed Mar. 30, 2012, James S. Cunningham.
U.S. Appl. No. 13/436,107, filed Mar. 30, 2012, Robert B. Stoddard.
U.S. Appl. No. 13/486,129, filed Jun. 1, 2012, Jason L. Craig.

* cited by examiner

ULTRASONIC SURGICAL INSTRUMENT

BACKGROUND

Technical Field

The present disclosure relates to ultrasonic surgical instruments and, more particularly, to ultrasonic surgical instruments that utilize selectively removable probe assemblies.

Background of Related Art

Laparoscopic surgical instruments are known in the medical arts. Laparoscopic devices may utilize RF energy, microwave energy, ultrasonic energy, thermal energy, resistive heating, etc. to effect tissue. For example, ultrasonic devices that are configured for use in laparoscopic surgical procedures, typically, include a housing, a handle assembly attached to the housing, a shaft extending from the housing, a probe/waveguide assembly extending within the shaft and coupleable to a torque adapter and a clamping jaw member positioned at a distal end of the shaft. The ultrasonic device may be configured to attach to a power supply via a power cable, or the ultrasonic device may be battery operated.

In the instance where the ultrasonic device is battery operated, one or more of the components associated with the ultrasonic device may be configured to selectively and removably connect to the ultrasonic device. For example, sometimes it is easier to ship the ultrasonic device in an unassembled configuration and have an end user assemble the ultrasonic device prior to use. Or, sometimes, one or more of the components associated with the ultrasonic device may be configured for use and sterilization for subsequent use thereof, or one or more components may be disposable, e.g., the probe assembly is typically disposable.

One component that lends itself to being selectively and removably connectable to the ultrasonic device is the probe assembly. In particular, the probe assembly is, typically, one of the longest components associated with the ultrasonic instrument, and as such, is sometimes shipped unattached to the housing. Moreover, the probe assembly, which supports an active blade thereon, is configured for use and subsequent sterilization thereof.

Conventional ultrasonic devices, typically, include a torque adapter that is configured to selectively and releasably connect to the probe assembly. Typically, a press-fit or friction fit connection couples the torque adapter and probe assembly to one another. Unfortunately, through use (and/or transportation), the functionality of the torque adapter may become compromised, e.g., the torque adapter does not provide a "tight" fit for the probe assembly, which, in turn, can result in the ultrasonic device not functioning properly or damage to the torque adapter and/or probe assembly.

SUMMARY

As can be appreciated, probe assemblies that are configured to quickly and easily couple to an ultrasonic instrument may prove advantageous in the surgical environment.

In the drawings and in the descriptions that follow, the term "proximal," as is traditional, will refer to an end which is closer to the user, while the term "distal" will refer to an end that is farther from the user.

An aspect of the present disclosure provides an ultrasonic surgical instrument. The ultrasonic surgical instrument includes a housing, a shaft, a probe and a rotating assembly. The shaft is supported on the housing and defines a longitudinal axis therethrough. The shaft supports a jaw member at a distal end thereof. The jaw member is movable between open and clamping configurations. The probe includes proximal and distal ends. The distal end has an active blade thereon configured to effect tissue when the jaw member is in the clamping configuration. The proximal end has at least one mating feature thereon. The rotating assembly operably supported on the housing is configured to rotate the shaft. The rotating assembly includes a torque adapter that is engageable with the at least one mating feature to selectively and releasably couple the probe to the housing.

The at least one mating feature may be in the form of a plurality of self tapping threads that are configured to displace material in the torque adapter to screw the probe into the torque adapter. The material in the torque adapter may be either metal or plastic.

The at least one mating feature may be in the form of a plurality of twist-lock features that are configured to engage a corresponding plurality of cavities on the torque adapter. In certain instances, the at least one mating feature is overmolded to the probe. In certain instance, the plurality of cavities on the torque adapter are disposed on interior surface thereof such that the plurality of twist-lock features on the probe fit into the corresponding cavities on the torque adapter such that rotation of the probe with respect to the torque adapter securely engages the twist-lock features and the cavities to one another to lock the probe into the torque adapter. In certain instance, a press-fit or wedge facilitates engagement between the twist-lock features on the probe and cavities in the torque adapter. The plurality of twist-lock features on the probe and cavities in the torque adapter may include a generally "L" configuration.

According to another aspect of the present disclosure, an ultrasonic surgical instrument is provided. The ultrasonic surgical instrument includes a housing, a shaft, a probe and a rotating assembly. The shaft is supported on the housing and defines a longitudinal axis therethrough. The shaft supports a jaw member at a distal end thereof. The jaw member is movable between open and clamping configurations. The probe is removably positionable within the shaft and has proximal and distal ends. The distal end has an active blade thereon configured to effect tissue when the jaw member is in a clamping configuration. The proximal end has a plurality self tapping threads machined on an exterior surface thereof. The rotating assembly is operably supported on the housing and configured to rotate the shaft including jaw member thereon. The rotating assembly includes a torque adapter that is selectively engageable with the probe. The plurality of self tapping threads is configured to penetrate the torque adapter to screw the probe thereinto and allow a user to selectively and releasably couple the probe to the housing.

According to yet another aspect of the present disclosure, an ultrasonic surgical instrument is provided. The ultrasonic surgical instrument includes a housing, a shaft, a probe and a rotating assembly. The shaft is supported on the housing and defines a longitudinal axis therethrough. The shaft supports a jaw member at a distal end thereof. The jaw member is movable between open and clamping configurations. The probe is removably positionable within the shaft and has proximal and distal ends. The distal end has an active blade thereon configured to effect tissue when the jaw member is in a clamping configuration. The proximal end has at least one twist-lock feature machined thereon. The rotating assembly is operably supported on the housing and configured to rotate the shaft including the jaw member. The rotating assembly includes a torque adapter having at least one a corresponding cavity disposed thereon. The at least one twist-lock feature on the probe is engageable with the at least one corresponding cavity on the torque adapter to selectively and releasably couple the probe to the housing.

The plurality of cavities on the torque adapter are disposed on interior surface thereof such that the plurality of twist-lock features on the probe fit into the corresponding cavities on the torque adapter such that rotation of the probe with respect to the torque adapter securely engages the twist-lock features and the cavities to one another to lock the probe into the torque adapter. In certain instance, a press-fit or wedge facilitates engagement between the twist-lock features on the probe and cavities in the torque adapter. The plurality of twist-lock features on the probe and cavities in the torque adapter may include a generally "L" configuration.

BRIEF DESCRIPTION OF THE DRAWINGS

Various embodiments of the present disclosure are described hereinbelow with references to the drawings, wherein.

DETAILED DESCRIPTION OF THE EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
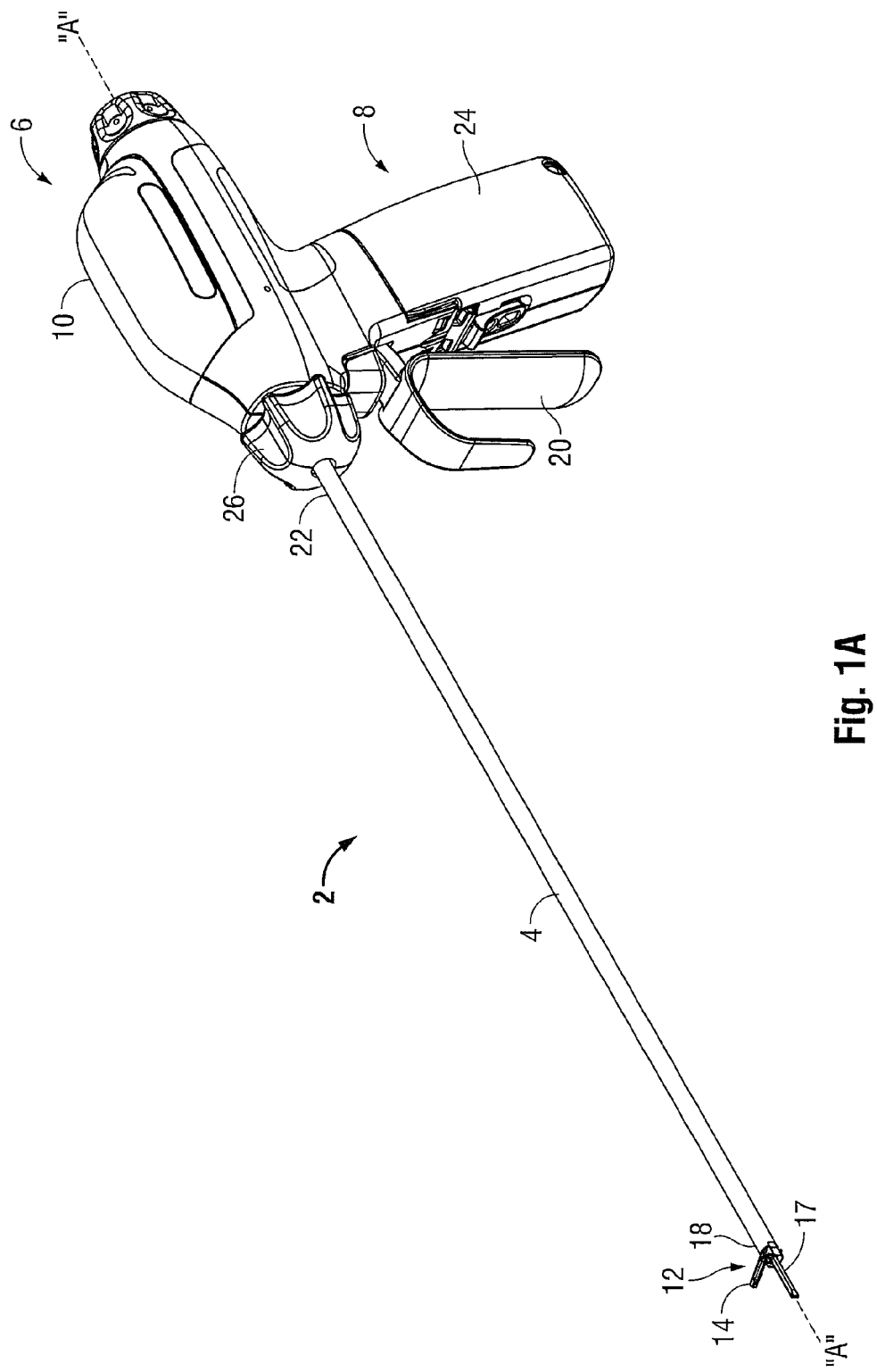
FIG. 1A is a side, perspective view of a battery powered ultrasonic surgical instrument configured for use with a selectively removable probe assembly according to an embodiment of the present disclosure.

With reference to FIGS. 1A-3, and initially with reference to FIG. 1A, a battery powered ultrasonic surgical instrument 2 configured for use with a selectively removable probe/waveguide assembly 16 (probe 16) according to an embodiment of the present disclosure is illustrated. Briefly, instrument 2 includes a housing 6 configured to house one or more components, e.g., transducer (not explicitly shown), probe 16 and electrical circuitry that is configured for electrical communication with a battery assembly 8 of the instrument 2. A proximal end of housing 6 is configured to releasably couple to an ultrasonic generator 10 and the battery assembly 8. A distal end of the housing 6 is configured to support and/or couple to a proximal end 22 of a shaft 4 (see FIG. 1B for example) having a longitudinal axis "A-A" defined therethrough. A rotation knob 26 operably couples to a torque adapter 28 (see FIG. 1B, for example) and is configured to rotate the shaft 4 approximately 360° in either direction about the longitudinal axis "A-A." An end effector 12 includes a jaw member 14 that is supported at a distal end 18 of the shaft 4 adjacent an active blade member 17 disposed at a distal end of the probe 16. Jaw member 14 functions as a "clamping jaw" and is movable relative to the active blade member 17 (and/or the distal end 18 of the shaft 4) between open and clamping configurations to clamp tissue when a lever or movable handle 20 is moved proximally. Jaw member 14 and active blade member 17 are configured to collectively grasp and ultrasonically treat tissue. Generator 10 includes the transducer that is coupled to the probe 16 via threads on the furthest proximal end of the probe and configured to produce motion at active blade member 17 of the probe 16. Battery assembly 8 includes a handpiece 24 having a battery (not explicitly shown) operably disposed therein.

Figure 1B:
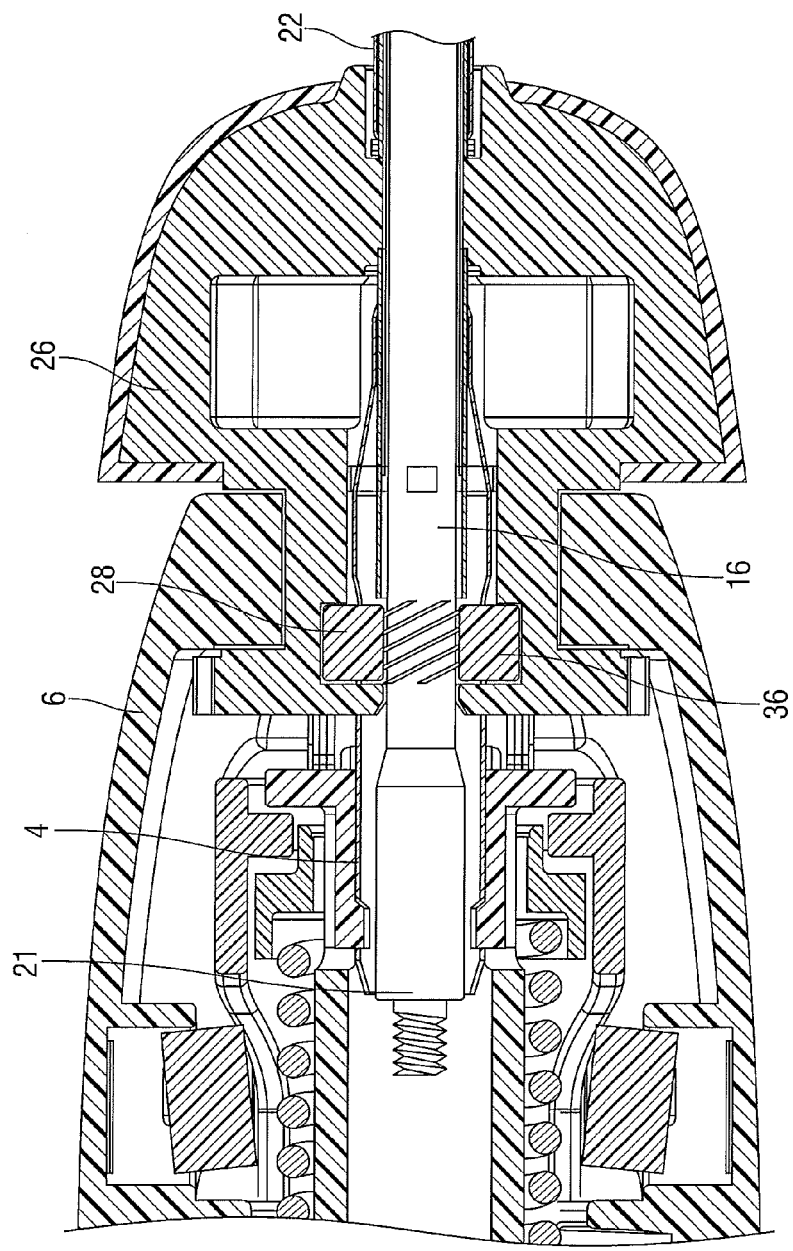
FIG. 1B is a side view illustrating internal components supported within a housing of the battery powered ultrasonic surgical instrument depicted in FIG. 1A.

Continuing with reference to FIG. 1B and also with reference to FIGS. 2-5, probe 16 is illustrated. Probe 16 may be made from any suitable material including, but not limited to metal, plastic, ceramic, etc. In the illustrated embodiments, probe 16 is made from metal.

Probe 16 extends within housing 6 and includes proximal end 21. Proximal end 21 is selectively and removably coupled to the torque adapter 28. In particular, proximal end 21 includes one or more mating features 30 (FIG. 2) thereon that are configured to engage or mate with one or more corresponding mating features on the torque adapter 28.

Figure 2:
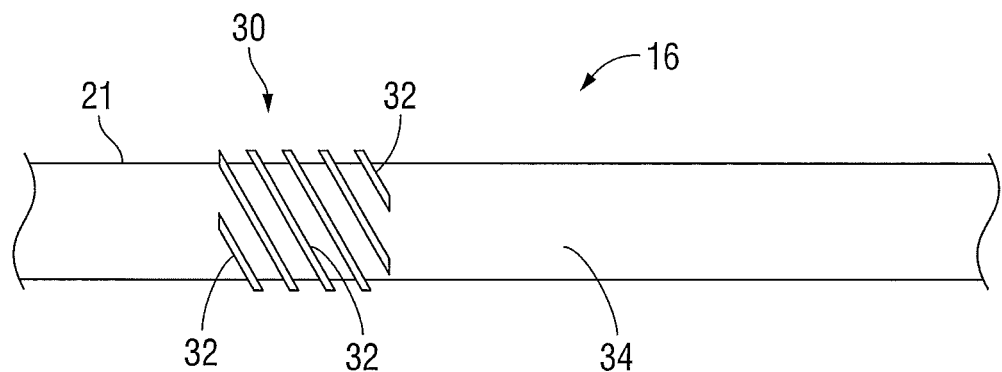
FIG. 2 is a side, perspective view of a proximal end of a probe depicted in FIG. 1B.

In particular, and in the embodiment illustrated in FIG. 2, mating feature 30 is in the form of a plurality of self tapping threads 32. Threads 32 extend along an exterior surface 34 of the probe 16 in the longitudinal direction. In accordance with the instant disclosure, the threads 32 should be minimized in the longitudinal direction and centered between nodes on probe 16.

Figure 3:
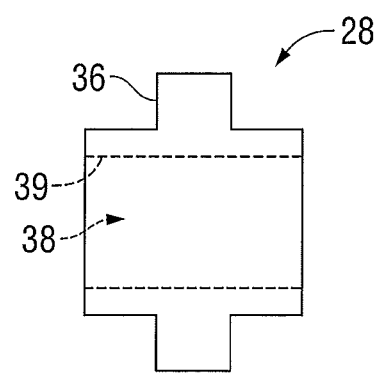
FIG. 3 is a side view of a torque adapter configured to selectively and releasably couple to the probe depicted in FIG. 2

Threads 32 may be positioned on the exterior surface 34 of the probe 16 by any suitable methods. For example, threads 32 may be machined into the exterior surface 34, overmolded onto exterior surface 34, etc. In the embodiment illustrated in FIG. 2, threads 32 are machined into the probe 16 and are configured to screw into the torque adapter 28 (FIG. 3). In some embodiments, the direction of the threads 32 can be in the clockwise direction or counter-clockwise direction, e.g., right or left hand twist.

Torque adapter 28 includes a generally circumferential configuration and operably couples to the rotating assembly 26. In particular, torque adapter 28 includes an outwardly extending flange 36 that is configured to couple the torque adapter 28 to the rotating assembly 26 (FIGS. 1B and 3). In embodiments, torque adapter 28 may be "pre-captured" or molded into the rotating assembly 26. In an assembled configuration, the torque adapter 28 facilitates transferring the rotational force provided by the rotating assembly 26 to the shaft 4.

An aperture 38 extends through the torque adapter 28 and is defined by a center portion 39 (e.g., a mating feature) that is configured to selectively and releasably couple to threads 32 (FIG. 3). Torque adapter 28 including center portion 39 is a unitary construction (i.e., made from a single material) and may be made from any suitable material. A suitable material is one that allows threads 32 to advance into the center portion 39 while allowing the threads 32 to create additional threads therein. Suitable materials include, but are not limited to plastic, metal, etc. In the illustrated embodiment, the center portion 39 is made from a relatively soft metal, e.g., copper. In embodiments, however, torque adapter 28 may be made from two or more materials. For example, and in one particular embodiment, an outer portion of the torque adapter 28 may be made from plastic and an inner portion of the torque adapter 28 may be made from metal. This embodiment is particularly useful when electrical isolation between the torque adapter 28 and one or more components of the instrument 2 is needed.

In use, the instrument 2 may be shipped in an unassembled configuration, e.g., the probe 16 is not coupled to the housing 6. To couple the probe 16 to the housing 6, proximal end 21 is positioned into an opening (see FIG. 1B for example) located at the distal end of the housing 6. Subsequently, a user screws the probe 16 into the torque adapter 28 via the threads 32 at the proximal end 21 thereof.

In the instance where the housing 6 and/or probe 16 need to be sterilized, the probe 16 may be unscrewed from the torque adapter 28 and the housing 6 and/or probe 16 including the active blade member 17 may be sterilized via one or more suitable sterilization methods, e.g., autoclave.

The unique configuration of the probe 16 including the threads 32 provided thereon allow a user to selectively remove the probe 16 from the housing 6 while overcoming the aforementioned drawbacks that are typically associated with conventional ultrasonic surgical instruments. That is, the threads 32 provide a "sure-fit" connection to the torque adapter 28 and the likelihood of engagement between the probe 16 and torque adapter 28 becoming compromised is reduced, if not eliminated.

Figure 4A:
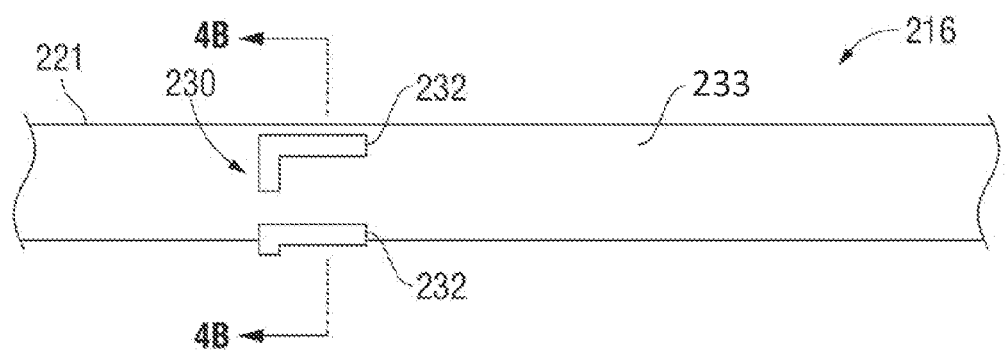
FIG. 4A is a side, perspective view of a proximal end of a probe according to another embodiment of the present disclosure.
Figure 4B:
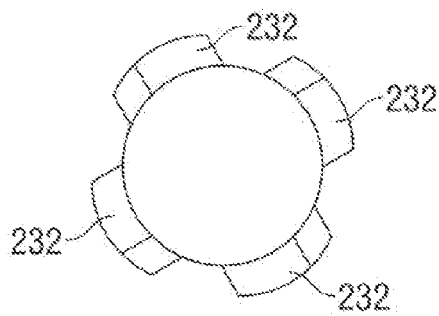
FIG. 4B is a cross-sectional view taken along line segment 4B-4B.
Figure 5:
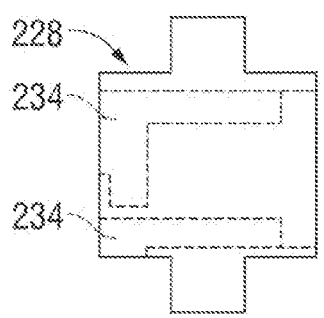
FIG. 5 is a side view of a torque adapter configured to selectively and releasably couple to the probe depicted in FIG. 4A.

FIGS. 4A-5, illustrate a probe 216 having a proximal end 221 with mating features 230 thereon. In the embodiment illustrated in FIGS. 4A-5, the mating features 230 are in the form of one or more twist-lock features 232 (a plurality of twist-lock features, e.g., 4, is shown). The twist-lock features 232 are configured to engage a corresponding plurality of cavities 234 on the torque adapter 228 (see FIGS. 4A-5). Similar to that of threads 32, twist-lock features 232 are machined into the exterior surface 234 of the probe 216. In the embodiment illustrated in FIG. 4A, the twist-lock features 232 extend from the exterior surface 233 and have a generally "L" configuration.

Cavities 234 on the torque adapter 228 are disposed on interior surface thereof and are shaped like the twist-lock feature 232 on the probe 216. In particular, the twist-lock features 232 fit into the corresponding cavities 234 such that rotation of the probe 216 with respect to the torque adapter 228 securely engages the twist-lock features 232 and cavities 234 to one another to lock the probe 216 into the torque adapter 228. While the probe 216 and torque adapter 228 have been described herein as including respective twist-lock features 232 and cavities 234, it is within the purview of the present disclosure that the probe 216 may include cavities 234 and the torque adapter 228 may include twist-lock features 232. The specific configuration of the probe 216 and torque adapter 228 may depend on manufacturer's preference, specific surgical procedure, etc.

In certain embodiments, a press-fit or wedge facilitates engagement between the twist-lock features 232 and cavities 234. In this instance, one or more surfaces that define the twist-lock features 232 and cavities 234 may be tapered or otherwise configured to facilitate engagement therebetween.

In use, referring also to FIG. 1A, the instrument 2 may be shipped in an unassembled configuration, e.g., the probe 216 is not coupled to the housing 6. To couple the probe 216 to the housing 6, the proximal end of the probe 216 is positioned into an opening (not explicitly shown) located at the distal end of the housing 6. Twist-lock features 232 are positioned within the corresponding cavities 234. Subsequently, a user twists the probe 216 with respect to the torque adapter 228 to lock the twist-lock features 232 into the cavities 234.

As can be appreciated, the probe 216 including the twist-lock features 232 disposed thereon overcomes the drawbacks typically associated with conventional surgical instruments.

From the foregoing and with reference to the various figure drawings, those skilled in the art will appreciate that certain modifications can also be made to the present disclosure without departing from the scope of the same. For example, overmolding can be used to secure the aforementioned torque adapters 28, 228 to the probes 16, 216. In this instance, positive or negative features (e.g., threads 32, twist-lock features 232, cavities 234) may be machined into the probes 16, 216 to secure an overmold material to the probes 16, 216. Suitable overmold material includes but is not limited to polycarbonate, ABS, PTFE or other suitable plastic that is compatible with the instruments 2, 102.

It is contemplated that the mating configurations described herein may be utilized with devices other than ultrasonic devices. For example, electrosurgical devices including RF surgical devices, microwave surgical devices, etc. that utilize selectively removable shaft assemblies may be configured for use with the mating configurations described herein. For example, it is contemplated that an exterior surface at a proximal end of a shaft of an endoscopic electrosurgical forceps may be modified to include one or more of the mating configurations, e.g., threads 32. As can be appreciated, certain modifications may need to be made to the endoscopic electrosurgical forceps to accommodate for the mating features provided on the shaft. For example, a device (or structure similar to one of the aforementioned torque adapters) may be provided in the housing or other component (e.g., a rotating assembly) of the endoscopic electrosurgical forceps and may be configured to selectively engage the one or more mating configurations provided on exterior surface at the proximal end of the shaft. For example, and in one particular embodiment, a portion of a distal end of the housing may be configured to engage the threads 32 to couple the shaft to the housing.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   a housing;
   a shaft supported by and extending from the housing and defining a longitudinal axis therethrough, the shaft supporting a jaw member at a distal end thereof, the jaw member movable between open and clamping configurations;
   a rotating assembly operably supported on the housing and coupled to the shaft for rotating the shaft relative to the housing;
   a torque adapter captured within and coupled to the rotating assembly; and
   a probe removably insertable into and releasably engageable with the rotating assembly, the probe including proximal and distal ends and defining an active blade at the distal end of the probe, the proximal end of the probe having at least one mating feature thereon, wherein the torque adapter is configured to releasably engage the at least one mating feature of the probe, wherein, once the probe is inserted into the rotating assembly, rotation of the torque adapter in a first direction relative to the probe locks the torque adapter and the probe in fixed longitudinal and rotational engagement to thereby releasably engage the probe with the rotating assembly, and wherein, with the torque adapter and the probe locked, rotation of the torque adapter in a second, opposite direction relative to the probe unlocks the torque adapter and the probe to permit withdrawal of the probe from the rotating assembly and the torque adapter.

2. An ultrasonic surgical instrument according to claim 1, wherein the at least one mating feature is machined into an exterior surface of the probe.

3. An ultrasonic surgical instrument according to claim 1, wherein the at least one mating feature is in the form of a plurality of self tapping threads that are configured to displace material in the torque adapter to screw the probe into the torque adapter.

4. An ultrasonic surgical instrument according to claim 3, wherein the material in the torque adapter is one of metal and plastic.

5. An ultrasonic surgical instrument according to claim 1, wherein the at least one mating feature is in the form of a plurality of twist-lock features that are configured to engage a corresponding plurality of cavities on the torque adapter.

6. An ultrasonic surgical instrument according to claim 5, wherein the plurality of cavities on the torque adapter are disposed on an interior surface thereof such that the plurality of twist-lock features on the probe fit into the corresponding cavities on the torque adapter and such that rotation of the probe with respect to the torque adapter securely engages the twist-lock features and the cavities to one another to lock the probe into the torque adapter.

7. An ultrasonic surgical instrument according to claim 6, wherein a press-fit or wedge facilitates engagement between the twist-lock features on the probe and the cavities in the torque adapter.

8. An ultrasonic surgical instrument according to claim 5, wherein the plurality of twist-lock features on the probe and the cavities in the torque adapter include a generally "L" configuration.

9. An ultrasonic surgical instrument according to claim 1, wherein the at least one mating feature is overmolded to the probe.

10. An ultrasonic surgical instrument, comprising:
a housing;
a shaft supported by and extending from the housing, the shaft defining a longitudinal axis therethrough, the shaft supporting a jaw member at a distal end thereof, the jaw member movable between open and clamping configurations;
a rotating assembly operably supported on the housing and coupled to the shaft for rotating the shaft relative to the housing;
a torque adapter captured within and coupled to the rotating assembly, the torque adapter having at least one cavity disposed thereon; and
a probe removably insertable into and releasably engagable with the rotating assembly, the probe including proximal and distal ends and defining an active blade at the distal end of the probe, the proximal end having at least one twist-lock feature machined thereon,
wherein the at least one twist-lock feature on the probe is configured to releasably engage the at least one cavity on the torque adapter, wherein, once the probe is inserted into the rotating assembly, rotation of the torque adapter in a first direction relative to the probe locks the torque adapter and the probe in fixed longitudinal and rotational engagement to thereby releasably engage the probe with the rotating assembly, and wherein, with the probe and the torque adapter locked, rotation of the torque adapter in a second, opposite direction relative to the probe unlocks the torque adapter and the probe to permit withdrawal of the probe from the rotating assembly and the torque adapter.

11. An ultrasonic surgical instrument according to claim 10, wherein the the at least one cavity on the torque adapter is disposed on an interior surface thereof such that the at least one twist-lock feature on the probe fits into the corresponding cavity on the torque adapter, and such that rotation of the probe with respect to the torque adapter securely engages the at least one twist-lock feature and the at least one cavity to one another to lock the probe into the torque adapter.

12. An ultrasonic surgical instrument according to claim 11, wherein a press-fit or wedge facilitates engagement between the at least one twist-lock feature on the probe and the at least one cavity in the torque adapter.

13. An ultrasonic surgical instrument according to claim 10, wherein the at least one twist-lock feature on the probe and the at least one cavity in the torque adapter include a generally "L" configuration.

* * * * *